United States Patent [19]

Disteldorf et al.

[11] Patent Number: 4,469,867
[45] Date of Patent: Sep. 4, 1984

[54] ISOCYANATOISOCYANURATES

[75] Inventors: Josef Disteldorf; Werner Hübel, both of Herne, Fed. Rep. of Germany

[73] Assignee: Chemische Werke Huls Aktiengesellschaft, Herne, Fed. Rep. of Germany

[21] Appl. No.: 454,633

[22] Filed: Dec. 30, 1982

[30] Foreign Application Priority Data

Dec. 30, 1981 [DE] Fed. Rep. of Germany ....... 3151855

[51] Int. Cl.³ .......................................... C07D 251/34
[52] U.S. Cl. .................................................. 544/222
[58] Field of Search ........................................ 544/222

[56] References Cited

U.S. PATENT DOCUMENTS 4,283,535  8/1981  Disteldorf et al. ................. 544/222
4,379,905  4/1983  Stemmler et al. .................. 544/222

Primary Examiner—John M. Ford
Attorney, Agent, or Firm—Oblon, Fisher, Spivak, McClelland & Maier

[57] ABSTRACT

Polyisocyanatoisocyanurates of the formula

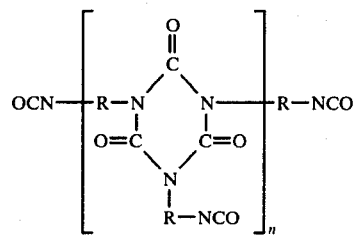

wherein the R groups may be the same or different and are aliphatic divalent radicals selected from the group consisting of divalent aliphatic radicals having the formulas

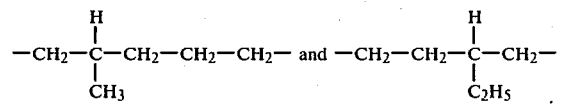

and n is a whole or fractional number from 1 to 5, are useful as isocyanate hardeners in polyurethane resin coatings.

5 Claims, No Drawings ns
ISOCYANATOISOCYANURATES

BACKGROUND OF THE INVENTION

1. Field of the Invention

This invention relates to polyisocyanate compounds containing isocyanurate groups and more particularly to such compounds which are prepared by trimerizing aliphatic diisocyanates.

2. Description of the Prior Art

The trimerization of hexamethylenediisocyanate (HDI) using various catalysts has been known for a long time and is described in a great number of patents. (cf. Accepted West German Specification Nos. 10 13 869, 12 03 792, 22 26 191; Unexamined West German Application No. 26 16 415; British Pat. Nos. 952,931, 966,338; U.S. Pat. Nos. 3,211,703, 3,330,828).

None of the processes described in these publications permit the problem-free production in a technically simple manner of practically colorless, low-viscosity, solvent-free polyisocyanates which are derived from HDI and contain isocyanurate groups.

The technical production of the isocyanatoisocyanurates based on HDI was first described in Unexamined West German Application No. 28 39 133. The products obtained with this process exhibit a viscosity less than 10,000 mPas at 25° C. and a NCO content of 18–24 weight %, especially from 20 to 23 weight percent, and represent valuable starting materials of the production of non-fading polyurethane varnishes.

However they have a disadvantage in that they have only a limited compatibility with the polyhydroxy compounds generally used in PUR varnishes and, furthermore, have a limited solubility in the frequently used non-polar solvents such as, for example, mineral spirits. Another disadvantage of these isocyanatoisocyanurates based on HDI is their only moderate thermal and oxidative stability, which becomes particularly obvious when lacquer films based on these compounds are overbaked.

Therefore a need has continued to exist for polyisocyanates containing isocyanurate groups based on aliphatic diisocyanates which are compatible with the polyhydroxy compounds conventionally used in PUR varnishes and which have good thermal and oxidative stability.

SUMMARY OF THE INVENTION

Accordingly, it is an object of this invention to provide polyisocyanatoisocyanurates which have good compability with polyhydroxy compounds conventionally used in polyurethane resin coatings.

A further object is to provide polyisocyanatoisocyanurates which have a good solubility in non-polar solvents.

A further object is to provide polyisocyanatoisocyanurates which have good thermal and oxidative stability.

A further object is to provide polyisocyanatoisocyanurates which have a high NCO content, relatively low vapor pressure, good photostability, and which are able to be used in solvent-free coating processes.

Further objects of the invention will become apparent in the description which follows:

The objects of the invention are obtained by a polyisocyanatoisocyanurate having the formula $$OCN-\left[R-N\begin{matrix}C=O\\/\ \ \ \backslash\\N\ \ \ \ \ N\\|\ \ \ \ \ \ \ |\\O=C\ \ \ C=O\\\backslash\ /\\N\\|\\R-NCO\end{matrix}R-NCO\right]_n$$

wherein the R groups may be the same or different and are aliphatic divalent radicals selected from the group consisting of divalent aliphatic radicals having the formulas $$-CH_2-\underset{CH_3}{\underset{|}{C}}-CH_2-CH_2-CH_2-\text{ and }-CH_2-CH_2-\underset{C_2H_5}{\underset{|}{C}}-CH_2-$$

and n is a whole or fractional number from 1 to 5.

The compounds of the invention are prepared by a process which comprises contacting an aliphatic diisocyanate selected from the group consisting of 2-methyl-1,5-pentane diisocyanate and 2-ethyl-1,4-butane diisocyanate with a trimerization catalyst.

DETAILED DESCRIPTION OF THE INVENTION AND PREFERRED EMBODIMENTS

The starting materials for preparing the compounds of the invention are mixtures of diisocyanates consisting essentially of a diisocyanate of the formula:

$$OCN-CH_2-\underset{H}{\underset{|}{C}}-CH_2-CH_2-CH_2-NCO$$
$$\overset{CH_3}{}$$

and a diisocyanate of the formula $$OCH-CH_2-CH_2-\underset{C_2H_5}{\underset{|}{C}}-CH_2-NCO$$
$$\overset{H}{}$$

Generally, the mixture of diisocyanates used in the process according to the invention is composed as follows: 88–99 weight percent of 2-methyl-1,5-pentane diisocyanate (MPDI), and 12–1 weight percent of 2-ethyl-1,4-butane diisocyanate (EBDI).

Pure 2-methyl-1,5-pentane diisocyanate can also be used instead of the mixture.

The preferred starting material is an appropriate mixture of diisocyanates of approximately 88 to 95 weight percent of 2-methyl-1,5-pentane diisocyanate and 12–5 weight percent of 2-ethyl-1,4-butane diisocyanate.

The preparation of the diisocyanates or mixture of diisocyanates is carried out by conventional methods by phosgenation of the corresponding diamines (cf. U.S. Pat. No. 3,631,198). These are obtained by catalytic hydrogenation of the corresponding dinitriles which, for example, accumulate as byproducts during the production of adiponitrile by reacting butadiene with HCN or by dimerizing acrylonitrile.

In principle, all of the known trimerization catalysts can be considered as trimerization catalysts for the process according to the invention. Thus, the aforementioned diisocyanates can readily be trimerized with sodium benzoate in dimethylformamide (DMF). [Chem. Abst. 60, 8332 (1963)] or with sodium phenolates in n-butyl acetate (British Pat. No. 1,386,399). However, the aforementioned catalysts must be removed from the reaction product. This drawback is overcome in Unexamined West German Application No. 28 21 109 by using as the catalyst as Mg- or Ca-salt of monohydroxyethylphthalic acid, which is incorporated into the reaction product. The catalysts which, upon completion of the trimerization process, can either be readily removed or are already completely deactivated during the reaction are especially suited for the production of the isocyanatoisocyanurates of the invention. Aziridine (and derivatives) in combination with a tertiary amine (Accepted West German Specification No. 12 03 792, Unexamined West German Application No. 23 25 862) is an example of such trimerization catalysts; further, the combination of an alkylene oxide and N,N'-endoethylene piperazine (Unexamined West German Application No. 25 44 684), as well as quaternary ammonium hydroxides (British Pat. No. 837,120) may be used.

The use of quaternary ammonium salts of organic acids of the following formula in accordance with Unexamined West German Application No. 29 16 201 has proven to be very well suited:

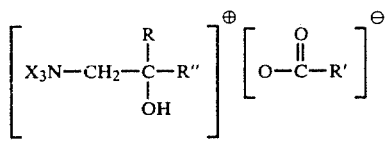

wherein X represents either the same or different aliphatic, cycloaliphatic, araliphatic or heterocyclic hydrocarbon groups of a quaternary ammonium nitrogen, or 2 X groups form with the quaternary nitrogen a ring containing one or more heteroatoms, or 3 X groups form a ring with the quaternary nitrogen by way of a common heteroatom, R can be an alkyl-, cycloalkyl- or aralkyl-group, and R and R" together can be a $C_1$-$C_{12}$-alkylene group, and R' can be a hydrogen, a hydroxyl group and a $C_1$-$C_{12}$-alkyl group, optionally containing a hydroxyl group, and R" can be either R or hydrogen.

The catalyst is added to the diisocyanate mixtures to be trimerized in amounts of 0.2 to 0.02 weight percent, preferably 0.08-0.04 weight percent; the trimerization is carried out within a temperature range of 40° to 140° C., preferably 60°-90° C. At these temperatures, the trimerization is complete within 1 to 60 minutes.

In the batchwise trimerization process of the diisocyanate mixture (MPDI+EBDI) in accordance with the invention, the diisocyanate mixture and 0.02 to 0.2 parts by weight of the catalyst described above are heated while stirring vigorously in a closed reaction vessel to 40°-60° C., but not over 140° C., preferably 70°-90° C. The course of the reaction is followed using the refractive index, which is a direct measure of the degree of conversion of the diisocyanate mixture or of the pure diisocyanate. At a conversion of approximately 30 to 45% calculated on the diisocyanate used, the reaction is terminated by cooling the reaction mixture to room temperature. At room temperature, such diisocyanate/isocyanurate mixtures have the required shelf life. The reaction mixture is then subjected to a thin-film evaporation at 150° C. and 0.1 Torr to separate the unconverted ingredients, i.e., the monomeric diisocyanate or mixture of diisocyanates, and the catalyst. The isocyanurates thus prepared in accordance with the invention have an NCO content of 19-24%, preferably 20.5 to 22.5% by weight, a monomer content of less than 0.7% by weight, and a viscosity below 12,000 mPas at 25° C.

The isocyanatoisocyanurates in accordance with the invention possess a number of advantageous properties which make them extremely suitable as isocyanate hardeners in coating systems using the isocyanatepolyaddition process. However, because of their low viscosity, which varies as a function of the degree of oligomerization, but in general, lies below 12,000 mPas (at 25° C.), only limited amounts of solvents, or none at all, are required for this applicaton.

The main advantage with respect to prior polyisocyanates lies in the improved compatibility of the compounds prepared in accordance with the invention with non-polar solvents, which significantly increases the range of applications for these compounds relative to conventional products. Moreover, the surprisingly good thermal and oxidative stability of the compounds in accordance with the invention is to be emphasized.

Having generally described the invention, a more complete understanding can be obtained by reference to certain specific examples, which are provided herein for purposes of illustration only and are not intended to be limiting unless otherwise specified.

A. PREPARATION OF THE AMMONIUM SALTS USED AS CATALYSTS

EXAMPLE A-1

232 grams of dipropylene glycol (DPG) and 90 grams of glacial acetic acid are placed in a one-liter, three-neck flask fitted with a stirrer, a reflux condenser, and a dropping funnel. Trimethylamine was then introduced into this mixture until its weight increased by 87 grams. Subsequently, 87 grams of propylene oxide (PO) were added slowly at 25° C., while stirring vigorously. On completion of the PO addition, the mixture was stirred overnight at room temperature, then the unconverted volatile materials were drawn off under vacuum over a six hour period at 45° C. A residue with a weight of 484 grams remained.

By using the preparative process described above, other compounds were prepared whose composition is listed in the following Table 1 (Examples A2 to A6).

TABLE 1

| | Trimerization Catalysts | | | |
|---|---|---|---|---|
| Example | Amine | Acid | Alklyene oxide | Solvent |
| $A_2$ | trimethylamine | acetic acid | propylene oxide | dipropylene glycol |
| $A_3$ | trimethylamine | formic acid | propylene oxide | dipropylene glycol |
| $A_4$ | N,N'—endoethylenepiperazine | formic acid | propylene oxide | none |
| $A_5$ | N—methylmorpholine | cyanoacetic acid | propylene oxide | dipropylene glycol |
| $A_6$ | trimethylamine | 2-ethyl hexanoic acid | propylene oxide | dipropylene glycol |

EXAMPLE A7

500 parts by weight of triethylenediamine and 500 parts by weight of propylene oxide were heated for eight hours at reflux. The reaction mixture grew increasingly darker with increasing reaction time. Once the reaction was completed, the conductivity of the mixture no longer changed.

EXAMPLE A8

500 parts by weight of triethylenediamine were dissolved in 500 parts by weight of dimethyl formamide. 500 parts by weight of propylene oxide were added to room temperature to this solution. The solution was then heated at 40° C. for 18 hours. Thereafter, the reaction was completed. During storage, the conductivity of this solution changed only insignificantly.

B. PREPARATION OF ISOCYANATOISOCYANURATES IN ACCORDANCE WITH THE INVENTION

EXAMPLE B1

500 parts by weight of MPDI (with approximately 6% EBDI) and 0.2 parts by weight of the catalyst according to Example A6 were mixed with one another at 80°, while stirring vigorously. An evolution of heat occurred immediately, causing the temperature of the reaction mixture to rise to 95° C. The reaction mixture was heated at this temperature for another 20 minutes. During this time, the NCO content dropped to 35.4 weight percent. The reaction mixture was distilled in a thin-film evaporator at 160° C. and 0.1 Torr in order to remove the uncoverted MPDI. The reaction product (the residue of the thin-film evaporation) had an NCO content of 20.5 weight percent and a monomer content of less than 0.7% by weight. At 25° C., the viscosity was 11,500 mPas.

EXAMPLE B2

1,000 parts by weight of MPDI and 0.1 part by weight of the catalyst described in Example A7 were reacted at 80° C. in accordance with the process described in B1. On completion of the partial trimerization, the reaction mixture had an NCO content of 38.2 weight percent. The isocyanatoisocyanurate isolated by thin-film distillation had an NCO content of 21.3 weight percent and a monomer content of 0.6 weight percent. At 25° C. the viscosity of this isocyanatoisocyanurate was 10,900 mPas.

EXAMPLE B-3

In a manner similar to Example B1, 1,000 parts by weight of MPDI and 0.15 part by weight of the catalyst described in A1 were reacted at 80° C. On completion of the partial trimerization, the reaction mixture had an NCO content of 41.1 weight percent. The isocyanatoisocyanurate isolated by thin-film distillation had an NCO content of 25.7 weight percent and a monomer content of 0.7 weight percent. At 25° the viscosity of the isocyanatoisocyanurate was 10,500 mPas.

Having now fully described the invention, it will be apparent to one of ordinary skill in the art that many changes and modifications can be made thereto without departing from the spirit or scope of the invention as set forth herein.

What is claimed as new and sought to be protected by Letters Patent of the United States is:

1. A compound of the formula

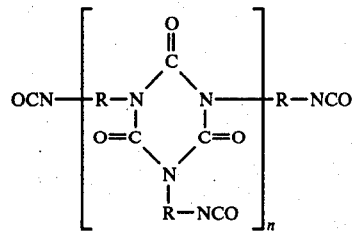

wherein the R groups may be the same or different and are aliphatic divalent radicals selected from the group consisting of divalent aliphatic radicals having the formulas

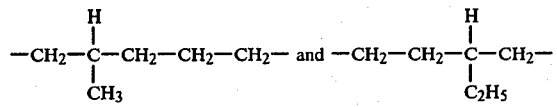

and n is a whole or fractional number from 1 to 5.

2. The compound of claim 1 wherein the NCO—content is 18 to 24% by weight.

3. The compound of claim 1 wherein the NCO—content is 20 to 23% by weight.

4. The compound of claim 1 wherein the monomer content is less than 0.7% by weight.

5. The compound of claim 1 wherein n is an integer from 1 to 5.

UNITED STATES PATENT AND TRADEMARK OFFICE
CERTIFICATE OF CORRECTION

PATENT NO. : 4,469,867

DATED : September 4, 1984

INVENTOR(S) : Disteldorf et al.

It is certified that error appears in the above-identified patent and that said Letters Patent is hereby corrected as shown below:

On the title page, Item [75] Inventors: add
--[75] Elmar Wolf of Recklinghausen, West Germany --

Signed and Sealed this

Twenty-second Day of January 1985

[SEAL]

Attest:

DONALD J. QUIGG

Attesting Officer     Acting Commissioner of Patents and Trademarks